United States Patent [19]
Green

[11] Patent Number: 4,994,073
[45] Date of Patent: Feb. 19, 1991

[54] SKIN FASTENER

[75] Inventor: David T. Green, Westport, Conn.

[73] Assignee: United States Surgical Corp., Norwalk, Conn.

[21] Appl. No.: 314,368

[22] Filed: Feb. 22, 1989

[51] Int. Cl.⁵ ............. A61B 17/00; F16B 15/02
[52] U.S. Cl. ............................... 606/220; 606/213; 411/457; 411/904; 411/920
[58] Field of Search ......... 128/334 C, 337, 92 YC; 411/457, 460, 469, 904, 920; 606/220, 213

[56] References Cited

U.S. PATENT DOCUMENTS

| | | | |
|---|---|---|---|
| 3,209,754 | 10/1965 | Brown | 606/221 |
| 3,273,562 | 9/1966 | Brown | 606/221 |
| 3,643,851 | 2/1972 | Green et al. | |
| 3,744,495 | 7/1973 | Johnson | 606/142 |
| 4,217,902 | 8/1980 | March | 606/221 |
| 4,402,445 | 9/1983 | Green | |
| 4,506,670 | 3/1985 | Crossley | |
| 4,523,591 | 6/1985 | Kaplan et al. | |
| 4,534,350 | 8/1985 | Golden et al. | 128/334 C |
| 4,570,623 | 2/1986 | Ellison et al. | 128/92 YC |
| 4,618,086 | 10/1986 | Li et al. | |
| 4,635,637 | 1/1987 | Schreiber | 128/337 |
| 4,667,674 | 5/1987 | Korthoff et al. | |
| 4,723,540 | 2/1988 | Gilmer, Jr. | 128/92 YC |
| 4,724,839 | 2/1988 | Bedi et al. | 128/334 C |
| 4,841,960 | 6/1989 | Garner | |
| 4,873,976 | 10/1989 | Schreiber | 128/334 R |

FOREIGN PATENT DOCUMENTS 458204 7/1950 Italy ..................... 411/494

OTHER PUBLICATIONS

U.S. patent application Ser. No. 7/201,841, filed Jun. 3, 1988 of Michael A. Oberlander.

Primary Examiner—Randall L. Green
Assistant Examiner—Gary Jackson
Attorney, Agent, or Firm—Thomas R. Bremer

[57] ABSTRACT

A surgical fastener for fastening layers of body tissue as in skin grafting procedures. The fastener comprises a backspan and at least two barbed prongs. The barbs are flat, triangular and are coplanar with respect to each other, as well as being in parallel alignment with the axis of the backspan. The surgical fastener is made of bioabsorbable material to eliminate the need for removal.

18 Claims, 9 Drawing Sheets

SKIN FASTENER

BACKGROUND OF THE INVENTION

1. Field of the Invention

This invention relates to fasteners, and particularly to surgical fasteners used to join body tissue.

2. Description of the Prior Art

Fasteners have been used surgically to eliminate the need for suturing, which is both time consuming and inconvenient. In many applications the surgeon can use a stapler apparatus, i.e., a fastener implanting device loaded with surgical fasteners to accomplish in a few seconds what would have taken many minutes to perform by suturing. This reduces blood loss and trauma to the patient. The terms "fastener" and "staple" are used interchangeably herein.

Surgical fasteners have been in the form of ordinary metal staples, which are bent by the delivery apparatus to hook together body tissue. Also, two-part fasteners have been used, as illustrated in U.S. Pat. No. 4,506,670 in which a barbed staple is used in conjunction with a retaining piece to hold the staple in place.

Typically, the two part staple comprises a back span and two barbed prongs which are engaged and locked into a separate retainer piece. In use, the staple is pressed into the body tissue so that the barbs penetrate the tissue and emerge from the other side where they are then locked into the retainer piece. The retainers prevent the staple from working loose from the tissue. The two piece fasteners cannot be unlocked and are not removable. For this reason, they must be made of a bioabsorbable material.

Korthoff, et al., U.S. Pat. No. 4,667,674, herein incorporated by reference, discloses a two part surgical fastener comprising a fastener member and a retainer member. The fastener member has a base, and a pair of prongs extending perpendicularly from the base. The prongs are spaced inward from the respective ends of the base in order to prevent splaying of the prongs, and to improve hemostasis.

The two piece fasteners require the staple delivery apparatus to have access to both sides of the tissue. Usually, such devices have a U-shaped member into which tissue is inserted. The stapler apparatus has a fastener holder and an anvil which are pivotally connected at one end, and mounted on the legs of the U-shaped support structure. See, for example, Green U.S. Pat. No. 4,402,445, which discloses a surgical fastener and means for applying same. In a surgical operation, the issue to be joined is positioned between the fastener holder and the anvil, which contains the fastener retainers. The fasteners are ejected from the holder into the tissue, and the prongs are locked into the retainers.

In some applications, however, it is not possible to have access to body tissue from two opposite directions. For example, in skin grafting applications one can only apply fasteners from a stapler positioned above the skin.

The prior art includes many examples of surgical staplers which do not enclose the body tissue between an anvil and fastener holder. For example, surgical staplers such as those described in U.S. Pat. No. 3,643,851 and U.S. Pat. No. 4,618,086 approach the skin from one direction. However, they require the use of staples which are malleable enough to be crimped by an anvil so that the prongs hook into the tissue. Typically, such staples are made of metal and are not bioabsorbable. They must be removed by another device, such as a stapler extractor. Furthermore, such staples are useful for joining tissue layers laterally, as for example in closing wounds in skin or fascia, but are not optimum for laminarly fastening one layer of tissue onto another, as in skin grafting.

Hence there is a need for a surgical fastener which is capable of being delivered into the surface of body tissue from one direction, which can join layers of tissue both laterally and laminarly as required in skin grafting applications, and which is bioabsorbable to eliminate the need for a separate and painful removal operation.

SUMMARY OF THE INVENTION

Accordingly, it is one object of this invention to provide a surgical fastener for joining body tissue.

It is another object of the present invention to provide a single piece fastener for joining one layer of body tissue to another layer.

It is yet a further object of the present invention to provide a surgical fastener which is bioabsorbable.

Still a further object of the present invention is to provide a surgical fastener in combination with an instrument for applying same.

These and other objects and advantages are provided for in a surgical fastener for joining layers of body tissue comprising a back span, and at least two prongs extending substantially perpendicularly from said backspan in substantially parallel relationship to each other, each prong having a shaft portion and at least one flat, substantially triangular shaped barb means for penetrating body tissue and retaining the fastener in the body tissue.

The surgical fastener of the present invention is optimally constructed of a bioabsorbable resinous material. A preferred resinous material, which is absorbable in the body, is disclosed in Kaplan et al., U.S. Pat. No. 4,523,591, hereby incorporated by reference.

Further features of the invention, its nature and various advantages will be more apparent from the accompanying drawings and the following detailed description of the invention.

DETAILED DESCRIPTION OF THE PREFERRED EMBODIMENTS

The skin fastener or skin tack disclosed herein can be used in conjunction with a surgical stapling instrument capable of propelling or implanting the skin fastener into the body tissue to be fastened. Generally such instruments will have a chamber for holding one or more fasteners, a means for storing and releasing power such as a spring, and a trigger means.

Figure 1A:
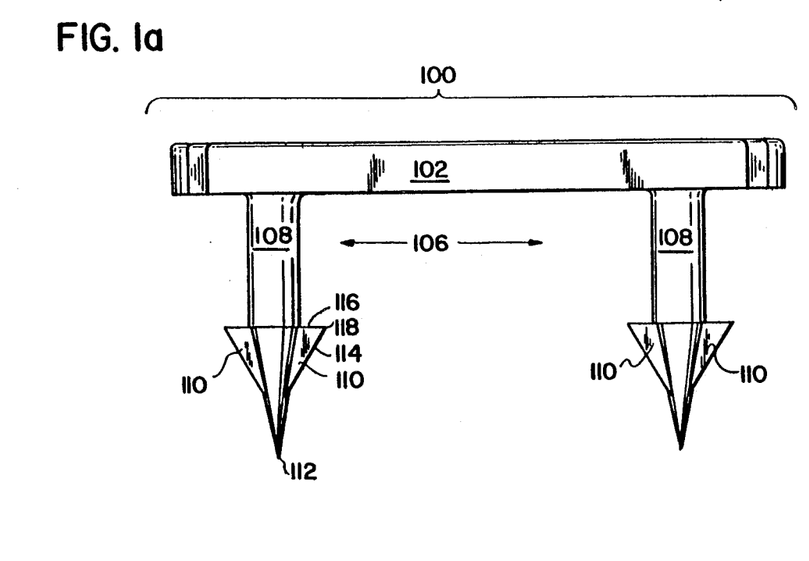
FIGS. 1a, 1b and 1c illustrate in side, bottom and end views respectively, an embodiment of the present invention.
Figure 1B:
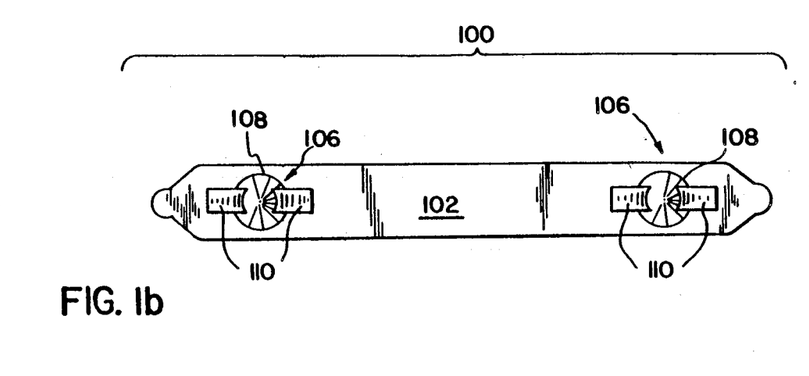
Figure 1C:
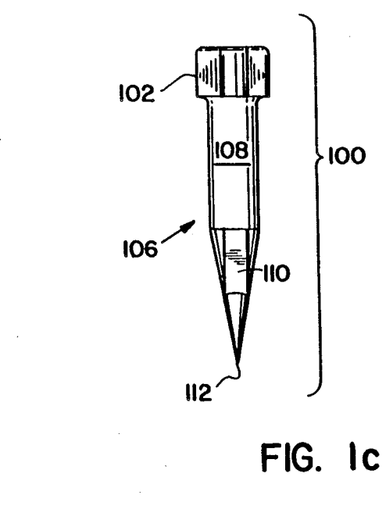

FIGS. 1a, 1b and 1c illustrate one embodiment of the present surgical fastener invention. FIGS. 1a, 1b, 1c show a two-pronged surgical fastener 100 with barbs 110 on each prong 106. Backspan or base 102 preferably is elongated and can have any shape adapted for its use in an instrument to receive and dispense it, such as the shape as shown, or a rectangular shape. Each prong 106 is an integral part of the fastener and projects substantially perpendicularly from the backspan 102 and in substantially the same direction as each other. The prongs 106 are substantially parallel to each other, and they are located in a spaced apart relationship from the ends of the backspan 102.

The skin tacking fastener of the present invention must function under operating conditions which limit the optimal shape of the prongs. For example the body tissue will be approached from only one direction, i.e., the target body tissue will not be clamped between an anvil and fastener holder. This means the tissue surrounding the fastener implant site will offer less lateral support to prevent bending or twisting. Also, the fastener of the present invention does not have a corresponding retainer portion which, in addition to holding the fastener, also helps to guide and align the fastener prongs as they enter the retainer openings.

Although the fastener of the present invention operates under conditions wherein it has less lateral support while entering the body tissue, one cannot compensate for this difficulty by fabricating it from an inherently strong material like stainless steel: the fastener must be bioabsorbable. Hence, one is presently limited to the strength of the bioabsorbable resins now known.

Prior art bioabsorbable resins such as those designed to lock into corresponding retainer pieces, are not optimally suitable for skin grafting since, because of the shape of their prongs, they encounter high resistance from the body tissue when entering.

It is important, then, for the shape of the prongs to maximize the strength of the prong for a given size fastener, yet minimize the body tissue resistance, while having a means to retain the fastener in the body tissue. Such attributes are achieved herein.

Each prong 106 is composed of a shaft portion 108 and at least one relatively thin substantially triangular shaped barb 110 which is flat on both sides to minimize body tissue resistance. Unlike those fasteners previously used in the art, the blade-like barbs 110 of the present fastener 100 not only puncture body tissue, but also slice through the tissue, thereby easing the entry of the fastener. The barbs 110 are in coplanar alignment with respect to each other and, where a pair of barbs 110 are mounted on a shaft portion 108, they are mounted on opposite sides of each shaft in parallel alignment with the lengthwise axis of the backspan 102. The tip 112 of each shaft 108 is preferably sharply pointed for piercing and entering skin or other body tissue.

The shafts 108 optimally are rounded near the backspan 102, and tapered into the tips 112. The shafts must be at least long enough to penetrate the layer of tissue to be joined and to allow the barbs 110 to become fully embedded in the underlying tissue. They are illustrated in this embodiment as being of equal length, but it is also within the scope of this invention to have unequally sized shafts and barbs. The base 116 of barbs 110 provides a means of retaining the fastener 100 in the body tissue by offering a flat surface highly resistant to movement of the barbs 110 in the direction rearward to that of the insertion of the barbs 110.

Vertices or corner edges 118 of the triangular barbs 110 are formed by the intersection of the base 116 and sides 114. Sides 114 facilitate the insertion of the barbs with minimal skin resistance, whereas vertices 118 further aid in retaining the barbs in the body tissue by digging into the tissue and offering high resistance to rearward movement of the barb.

Figure 2A:
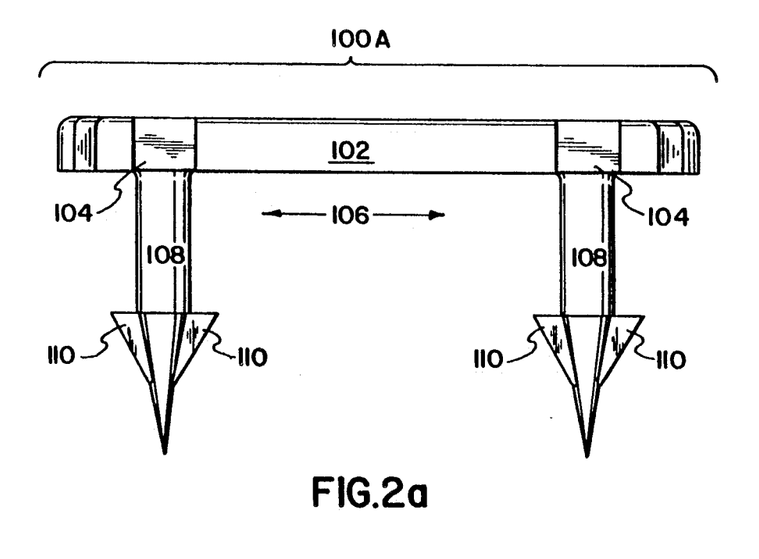
FIGS. 2a, 2b and 2c illustrate in side, bottom and end views respectively an alternative embodiment the invention having side indentations.
Figure 2B:
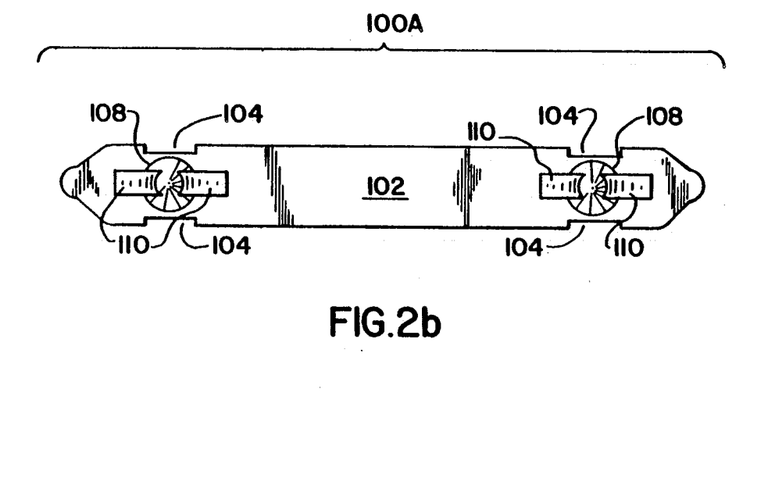
Figure 2C:
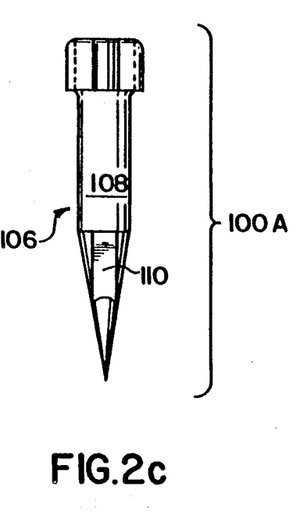

FIGS. 2a, 2b, 2c illustrate an alternative embodiment of the present surgical fastener invention 100A including optional indentations 104 in the backspan 102 on both sides of the prongs 106. These indentations 104 can cooperate with rail members in a fastener implanting instrument so as to minimize the possibility of the prongs' bending or twisting as they enter body tissue.

Figure 3A:
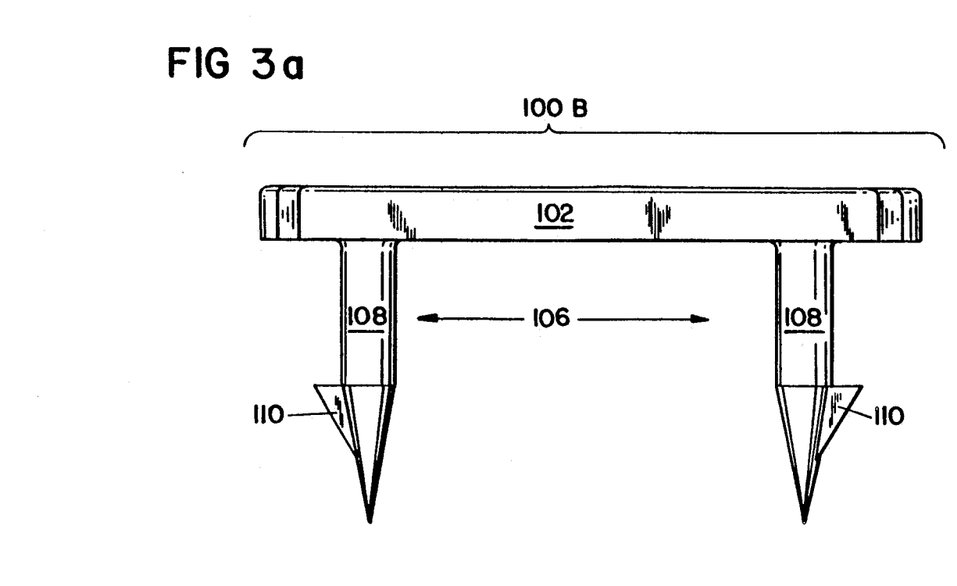
FIGS. 3a, 3b and 3c illustrate in side, bottom and end views respectively an alternative embodiment of the present invention having a barb on only one side of each prong.
Figure 3B:
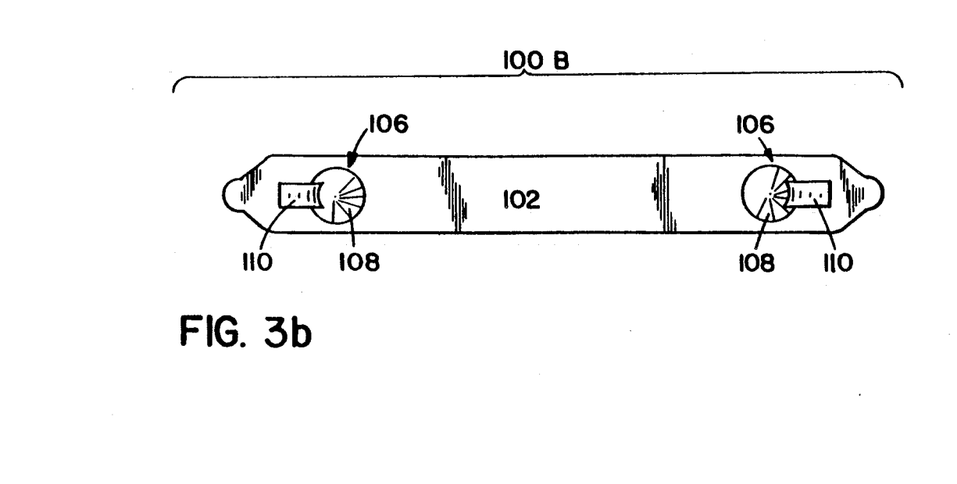
Figure 3C:
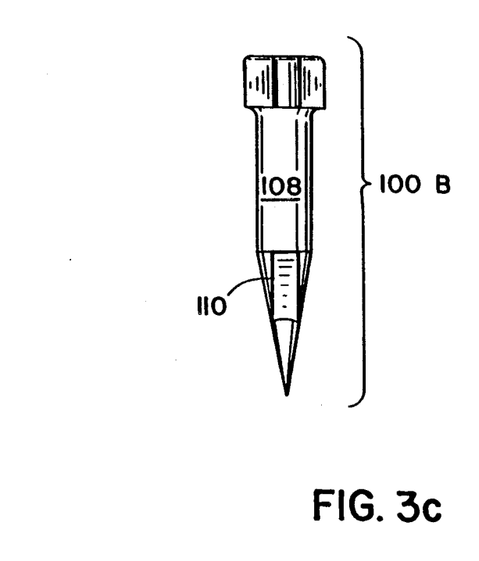

FIGS. 3a, 3b, 3c illustrate an alternative embodiment 100B of the present surgical fastener invention including a single 110 on each prong, the barb 110 projecting from only one side of the shaft 108.

Figure 4A:
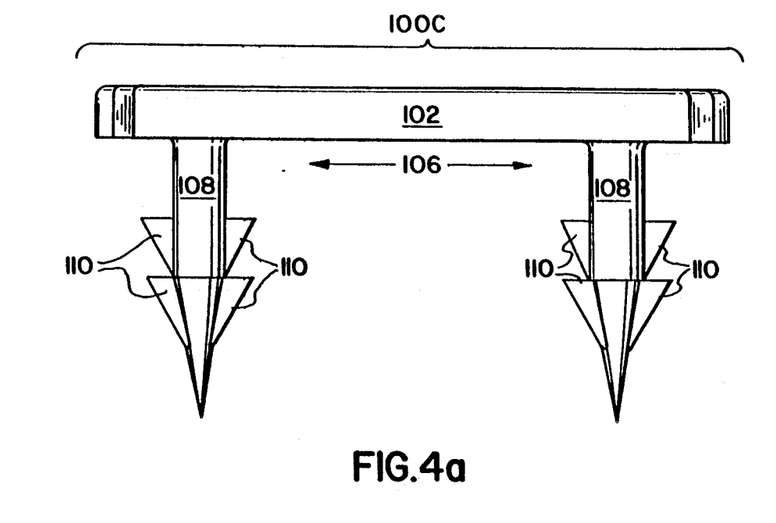
FIGS. 4a, 4b and 4c illustrate in side, bottom and end views respectively, an alternative embodiment of the invention having multiple rows of barbs on each prong.
Figure 4B:
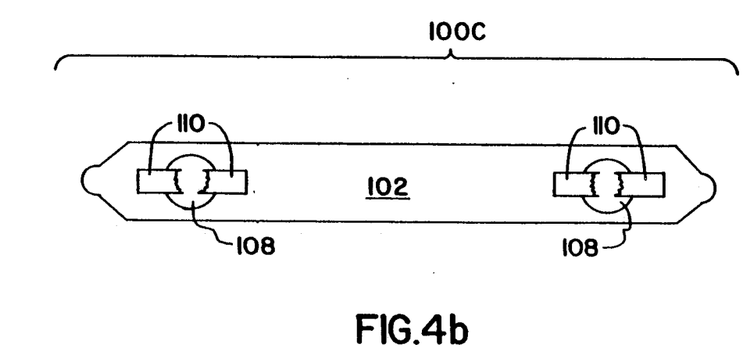
Figure 4C:
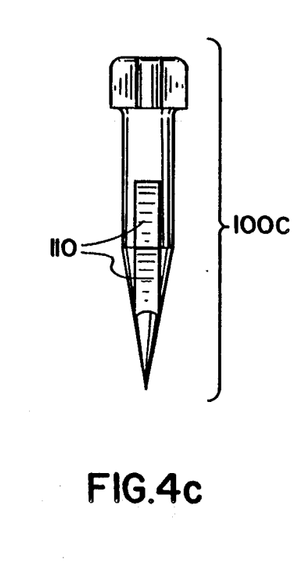

FIGS. 4a, 4b, 4c illustrate an alternative embodiment 100c of the present surgical fastener invention including multiple rows of barbs 110 on each prong 106.

Figure 5A:
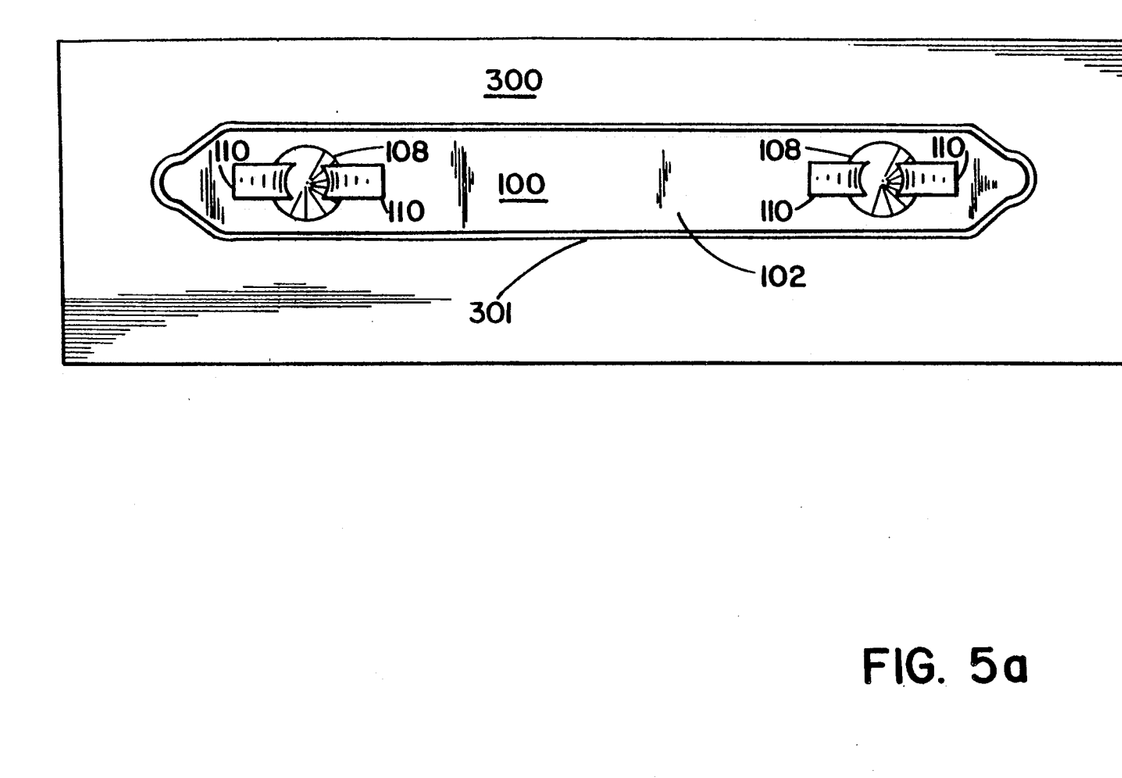
FIGS. 5a and 5b illustrate a view of the fastener of the present invention within the ejection chamber of a fastener implanting instrument.
Figure 5B:
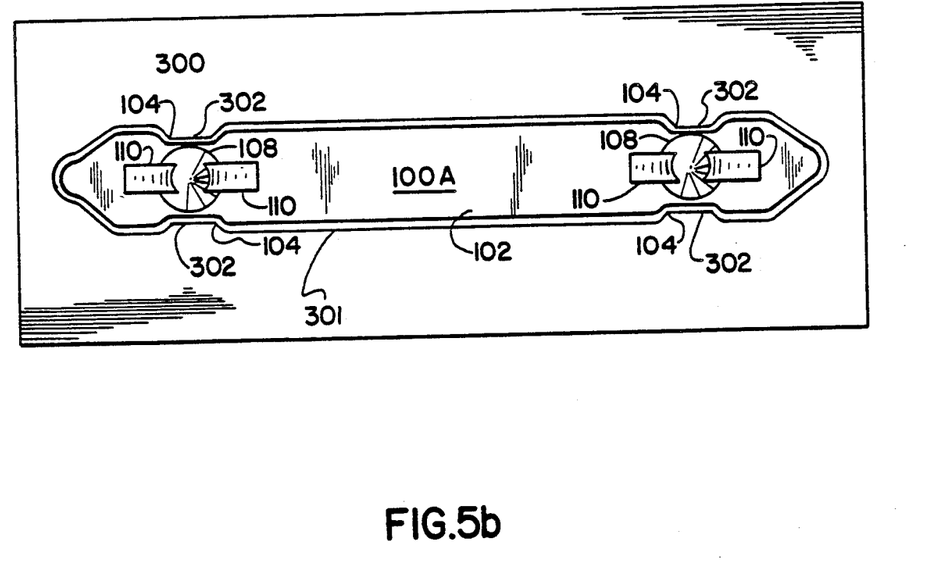

FIGS. 5a and 5b illustrate an end view of fasteners 100 and 100A inside an ejection chamber 300 of a surgical stapling apparatus. Fasteners 100 and 100A have prongs 106 pointing towards the exit opening 301. Rail members 302 in FIG. 5b cooperate with indentations 104 of fastener 100A to keep fastener 100A aligned as it is pushed through chamber 300, thereby reducing the possibility of fastener 100A jamming inside the instrument. Also, rails 302 project towards both of the flat sides of barbs 110 thereby deterring them from bending or twisting when they contact the body tissue to be fastened.

It should be realized that indentations 104, and cooperating rail members 302, are optional features which aid in implanting the skin fastener 100, but are not mandatory with respect to the fastener's function of piercing and holding body tissue.

Figure 6:
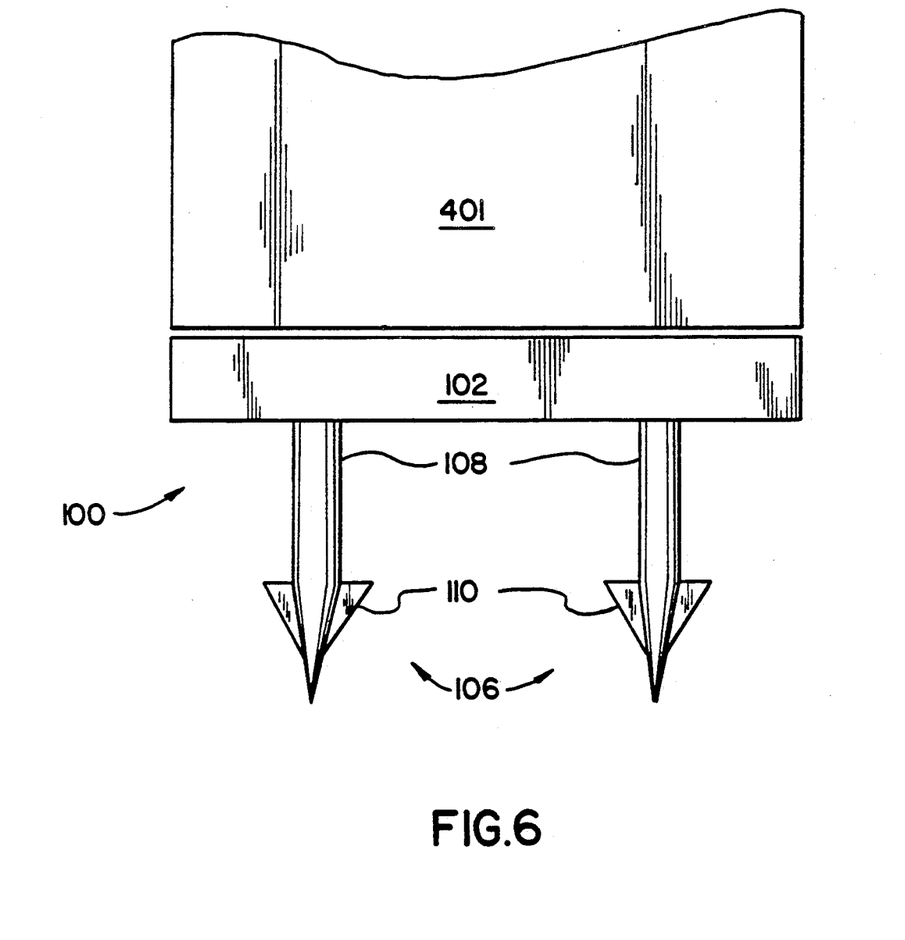
FIG. 6 illustrates a side view showing the fastener of the present invention in conjunction with a pusher member of a fastener implanting instrument.

FIG. 6 illustrates a side view showing the fastener 100 in conjunction with a pusher member 401 of a surgical stapling instrument (entire instrument not shown). Such instruments generally have a means to hold one or more fasteners, a trigger means, a means for storing and releasing power such as a spring means, and a drive means to drive the surgical fastener into the tissue. The drive means generally includes a pusher member, such as illustrated in FIG. 4 to push the fastener through an ejection chamber into the body tissue to be fastened.

Figure 7:
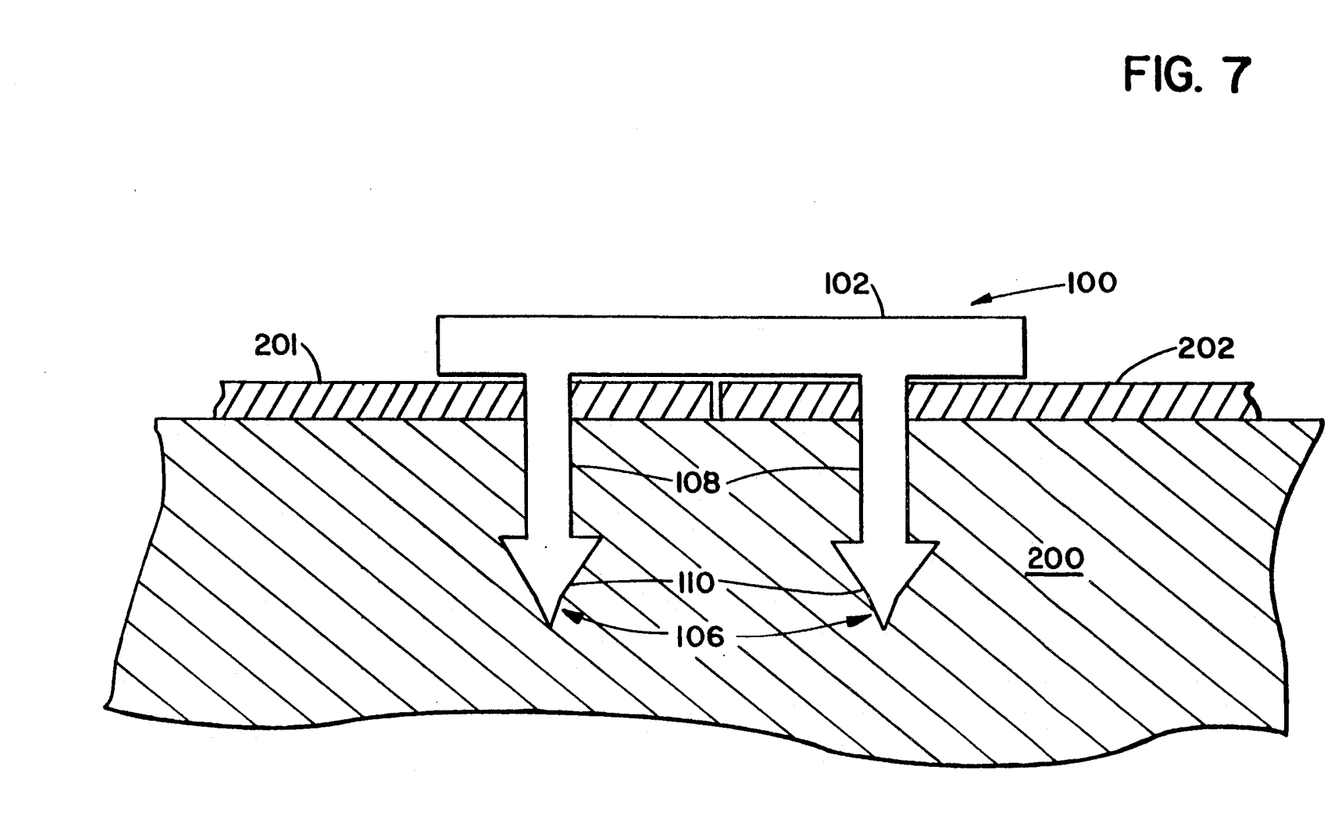
FIG. 7 illustrates a sectional side view showing the implanted fastener in use.
Figure 8:
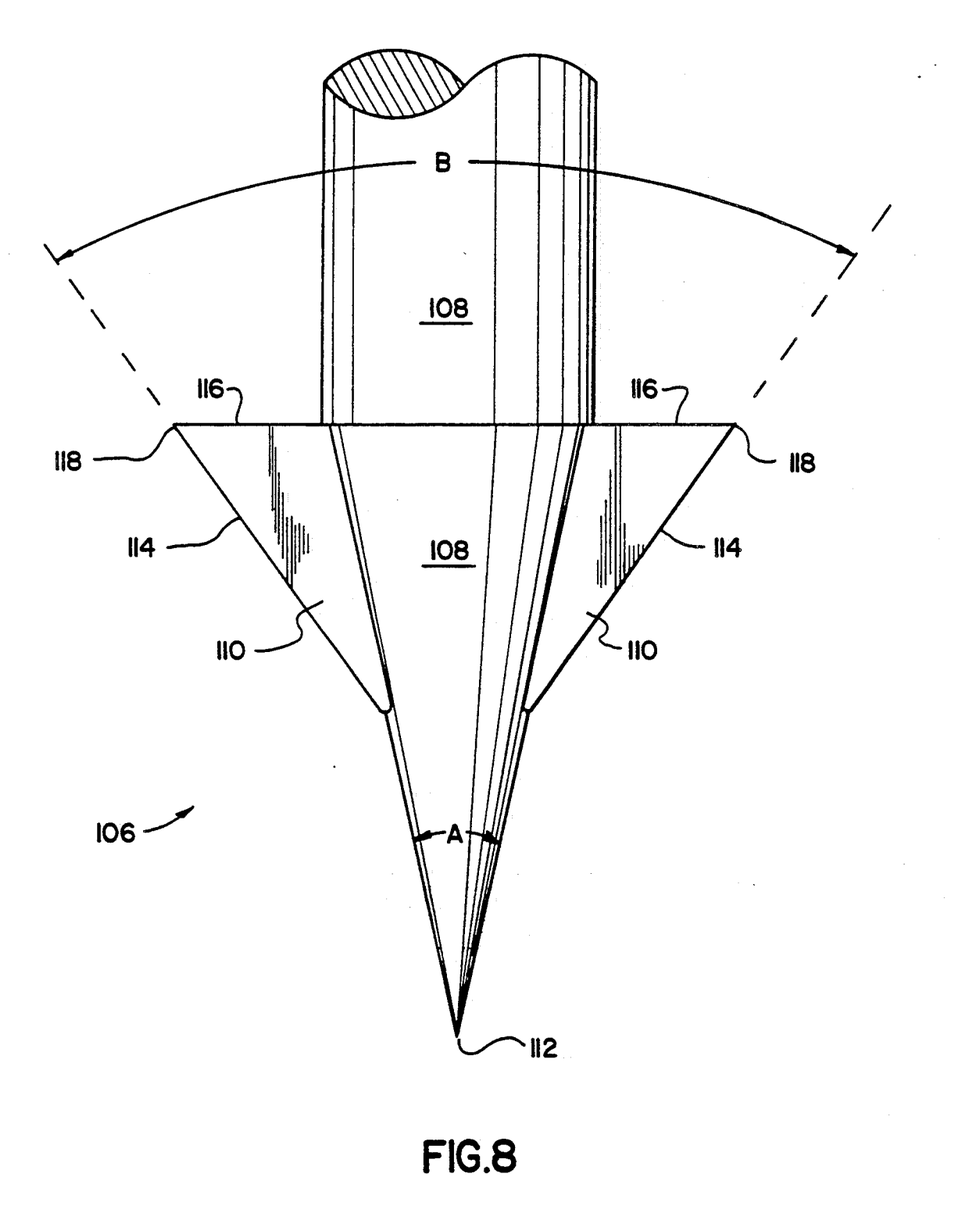
FIG. 8 shows a detailed view of the prong of the present fastener invention.

FIG. 7 illustrates the fastener in use. Fastener 100 is embedded in layers of body tissue for grafting skin. Grafted skin 201 is penetrated by a barb and fastened onto base tissue 200. Surrounding skin 202 is penetrated by a second barb. This illustration shows how tissue may be joined in two ways by the present invention laterally, by bridging the edges of grafted tissue 201 to surrounding tissue 202, and laminarly by pinning a grafted layer 201 onto an underlying base layer of tissue 200. The barbs 110 will not allow the fastener to fall out or be withdrawn The fastener of the present invention may have any dimensions suitable for the purpose of fastening body tissue. For example, in one embodiment of the fastener of the present invention it has been found useful to provide a backspan 102 with a length of about 0.39 inches, a width of about 0.045 inches, and a depth of about 0.034 inches, although other dimensions may also be used. As illustrated in FIG. 7, the length of shaft 108 is typically greater than the depth of grafted tissue 201 and surrounding tissue 202, in order to penetrate the underlying tissue 200 sufficiently, thereby allowing barbs 110 to obtain a firm setting. Thus, in the embodiment being discussed, shaft 108 may be about 0.167 inches from the backspan to the tip. The distance between the center points of the shafts 108 are generally about 0.25 inches, and the distance between the center point of the shaft 108 and the end of the backspan 102 is about 0.07 inches. As shown in FIG. 8, the angle A of the tip 112 of shaft 108 is preferably about 21°. The angle B formed by the edges of the barbs 110 is preferably about 64°. Side 114 of barb 110 intersects with the tapered portion of shaft 108 at a point about 0.041 inches from the tip 112 of shaft 108. Base 116 of barb 110 preferably extends about 0.018 inches from shaft 108 to vertex 118. The distance between the base 116 and the point at which side 114 intersects with shaft 108 is about 0.042 inches, and the distance between the backspan 102 and the base 116 is about 0.084 inches. As stated above however, other dimensions are obviously suitable in the practice of the present invention.

Because the fastener 100 cannot be easily removed, it is made of a bioabsorbable material such as copolymers of lactide and glycolide, or other bioabsorbable polymer materials. A preferred bioabsorbable resinous material for constructing the surgical fastener of the present invention is disclosed in Kaplan et al., U.S. Pat. No. 4,523,591. Fasteners of the present invention may be formed by injection molding of the bioabsorbable materials.

While the above description contains many specifics, these specifics should not be construed as limitations on the scope of the invention, but merely exemplifications of preferred embodiments thereof. Those skilled in the art will envision other possible variations that are within the scope and spirit of the invention as defined by the appended claims.

What is claimed is:

1. A surgical fastener for joining layers of body tissue comprising:
    (a) a backspan; and
    (b) at least two prongs spaced apart from the ends of said backspan extending substantially perpendicularly from said backspan in substantially parallel relationship to each other, each prong having a shaft portion with a tip portion tapering into a distal point and at least one, substantially triangular shaped barbed means for penetrating body tissue and retaining the fastener in the body tissue, said barbed means being located on the tapered tip portion of said shaft and having a distal edge spaced apart from said distal point, said barbed means further being disposed in the body tissue without passing completely therethrough for retaining the fastener in the body tissue without engaging a retainer.

2. The surgical fastener of claim 1 wherein the fastener is made of bioabsorbable material.

3. The surgical fastener of claim 2 wherein the bioabsorbable material is a resinous material.

4. The surgical fastener of claim 3 wherein the resinous bioabsorbable material is a copolymer of lactide and glycolide.

5. The surgical fastener of claim 1 wherein each barb means is flat on both sides.

6. The surgical fastener of claim 5 wherein the barb means are in coplanar alignment in relation to each other.

7. The surgical fastener of claim 1 wherein the barb means has vertex and a base for retaining the fastener in the body tissue by resisting movement of the barb means in a direction rearward to that of the insertion of the barb means.

8. A surgical fastener for joining layers of body tissue, comprising:
    (a) a backspan;
    (b) at least two prongs extending substantially perpendicularly from said backspan in substantially parallel relationship to each other and spaced apart from the ends of the backspan, each prong having a shaft portion, with a tip portion tapering into a distal point and at least one, substantially triangular shaped barb means for penetrating body tissue and retaining the fastener in the body tissue, said barbed means being located on the tapered tip portion of said shaft and having a distal edge spaced apart from said distal point,
    said barb means being flat on both sides and in coplanar alignment in relation to each other and having a base for resisting movement of the barb in a rearward direction opposite the direction of insertion of the barb means.

9. In combination:
    a surgical stapler having means for applying surgical fasteners; and
    at least one surgical fastener for joining layers of body tissue, said surgical fastener comprising a backspan, and at least two prongs spaced apart from the ends of said backspan extending substantially perpendicularly from said backspan in substantially parallel relationship to each other and in the same direction as each other, each prong having a shaft portion with a tip portion tapering into a distal point, and at least one substantially triangular shaped barbed means for penetrating body tissue and retaining said surgical fastener in the body tissue, said barbed means being located on the tapered tip portion of said shaft and having a distal edge spaced apart from said distal point, said barbed means being further disposed in the body tissue without passing completely therethrough for retaining the fastener in the body tissue without engaging a retainer.

10. The combination of claim 9 further comprising a pusher member for propelling the surgical fastener.

11. The combination of claim 9 wherein the surgical fastener is made of bioabsorbable material.

12. The combination of claim 11 wherein the bioabsorbable material is a resinous material.

13. The combination of claim 12 wherein the bioabsorbable resinous material is a copolymer of lactide and glycolide.

14. The combination of claim 9 wherein each barb means is flat on both sides.

15. The combination of claim 14 wherein the barb means are in coplanar alignment with each other.

16. The combination of claim 9 wherein each barb means has a vertex and a base for retaining the fastener in the body tissue by resisting movement of the barb in a direction rearward to that of the insertion of the barb means.

17. A surgical fastener for grafting skin comprising:
(a) a backspan; and
(b) at least two prongs spaced apart from the ends of said backspan in substantially parallel relationship to each other, each prong having a shaft portion with a tip portion tapering into a distal point and at least one substantially triangular shaped barbed means for penetrating through a skin graft material into body tissue, said barbed means being located on the tapered tip portion of said shaft and having a distal edge spaced apart from said distal point, said fastener being retained in said body tissue without passing completely therethrough to engage a retainer.

18. The surgical fastener of claim 17 wherein a first prong penetrates through said skin graft material into said body tissue, and a second prong penetrates through surrounding skin into said body tissue, thereby laminarly supporting said skin graft material against said body tissue and laterally supporting said skin graft material to said surrounding skin.

* * * * *